US009757009B2

(12) United States Patent
Sato et al.

(10) Patent No.: US 9,757,009 B2
(45) Date of Patent: Sep. 12, 2017

(54) IN VIVO INFORMATION ACQUIRING APPARATUS

(71) Applicant: OLYMPUS CORPORATION, Tokyo (JP)

(72) Inventors: Ken Sato, Nagano (JP); Fukashi Yoshizawa, Ina (JP); Naohito Doi, Nagano (JP)

(73) Assignee: OLYMPUS CORPORATION, Tokyo (JP)

( * ) Notice: Subject to any disclaimer, the term of this patent is extended or adjusted under 35 U.S.C. 154(b) by 483 days.

(21) Appl. No.: 13/858,368

(22) Filed: Apr. 8, 2013

(65) Prior Publication Data

US 2013/0225927 A1    Aug. 29, 2013

Related U.S. Application Data

(63) Continuation of application No. PCT/JP2011/069159, filed on Aug. 25, 2011.

(30) Foreign Application Priority Data

Oct. 8, 2010    (JP) .................................. 2010-228972

(51) Int. Cl.
*A61B 1/00* (2006.01)
*A61B 1/04* (2006.01)
(Continued)

(52) U.S. Cl.
CPC ...... *A61B 1/00006* (2013.01); *A61B 1/00016* (2013.01); *A61B 1/00036* (2013.01);
(Continued)

(58) Field of Classification Search
USPC .................................. 600/118, 117, 178, 160
See application file for complete search history.

(56) References Cited

U.S. PATENT DOCUMENTS

| 2004/0253304 | A1* | 12/2004 | Gross | ..................... | A61B 1/041 424/451 |
| 2005/0049488 | A1* | 3/2005 | Homan | .............. | A61B 1/00036 600/431 |

(Continued)

FOREIGN PATENT DOCUMENTS

| EP | 1 665 976 A1 | 6/2006 |
| JP | 2005-080841 | 3/2005 |

(Continued)

OTHER PUBLICATIONS

Extended Supplementary European Search Report dated Sep. 17, 2015 from related European Application No. 11 83 0453.4.

*Primary Examiner* — John P Leubecker
*Assistant Examiner* — Rajaa El Alami
(74) *Attorney, Agent, or Firm* — Scully, Scott, Murphy & Presser, P.C.

(57) ABSTRACT

A capsule endoscope includes, inside a capsule casing, an information acquiring section that acquires information on an inside of a body of a subject, a battery that supplies power, a detection section that, upon detection of introduction to the inside of the body of the subject, outputs a detection signal, a signal receiving section that receives a control signal from an outside and outputs an internal signal, and a control section that controls power supply from the battery to the information acquiring section according to the internal signal and the detection signal.

13 Claims, 9 Drawing Sheets

(51) Int. Cl.
*A61B 5/07* (2006.01)
*A61B 5/053* (2006.01)

(52) U.S. Cl.
CPC .............. *A61B 1/041* (2013.01); *A61B 5/073* (2013.01); *A61B 5/0538* (2013.01); *A61B 2560/0204* (2013.01); *A61B 2560/0266* (2013.01)

(56) References Cited

U.S. PATENT DOCUMENTS

| | | | |
|---|---|---|---|
| 2005/0054897 A1 | 3/2005 | Hashimoto et al. | |
| 2005/0064815 A1 | 3/2005 | Kanazawa | |
| 2005/0065407 A1* | 3/2005 | Nakamura | A61B 1/00016 600/160 |
| 2006/0264734 A1* | 11/2006 | Kimoto | A61B 1/00016 600/407 |
| 2007/0161851 A1* | 7/2007 | Takizawa | A61B 1/00156 600/102 |
| 2008/0033242 A1* | 2/2008 | Tamura | A61B 1/00009 600/109 |
| 2008/0076965 A1* | 3/2008 | Yoshizawa | A61B 1/00016 600/103 |
| 2008/0108865 A1* | 5/2008 | Tamura | A61B 1/041 600/101 |
| 2008/0306360 A1* | 12/2008 | Robertson | A61B 1/00016 600/302 |
| 2009/0076352 A1* | 3/2009 | Fujita | A61B 1/00016 600/302 |
| 2009/0253954 A1* | 10/2009 | Katayama | A61B 1/045 600/103 |
| 2009/0264702 A1* | 10/2009 | Yoshizawa | A61B 5/073 600/117 |
| 2009/0275801 A1* | 11/2009 | Sakai | A61B 1/00032 600/117 |
| 2009/0292167 A1* | 11/2009 | Kimoto | A61B 1/00016 600/109 |
| 2010/0145149 A1* | 6/2010 | Yoshida | A61B 1/041 600/118 |
| 2010/0268026 A1* | 10/2010 | Takizawa | A61B 1/00158 600/109 |
| 2010/0275934 A1* | 11/2010 | Keren | G01D 5/2066 128/899 |

FOREIGN PATENT DOCUMENTS

| | | | | |
|---|---|---|---|---|
| JP | 2005-081005 A | | 3/2005 | |
| JP | 2005-110932 | | 4/2005 | |
| JP | 2005-237460 A | | 9/2005 | |
| JP | 2006-109942 | | 4/2006 | |
| JP | 2010-094442 | * | 10/2008 | |
| JP | 2009-089907 | | 4/2009 | |
| JP | 3151662 | | 6/2009 | |
| JP | 2010-094442 | | 4/2010 | |
| JP | WO 2013015018 A1 | * | 1/2013 | ......... A61B 1/00036 |
| WO | WO 2005/023102 A1 | | 3/2005 | |

* cited by examiner

IN VIVO INFORMATION ACQUIRING APPARATUS

CROSS REFERENCE TO RELATED APPLICATION

This application is a continuation application of PCT/JP2011/069159 filed on Aug. 25, 2011 and claims benefit of Japanese Application No. 2010-228972 filed in Japan on Oct. 8, 2010, the entire contents of which are incorporated herein by this reference.

BACKGROUND OF THE INVENTION

1. Field of the Invention

Embodiments of the present invention relate to an in vivo information acquiring apparatus that is introduced to an inner portion of a subject and acquires information on an inside of a body.

2. Description of the Related Art

In recent years, in the field of endoscopes, in vivo information acquiring apparatuses, which are swallow-type capsule endoscopes, have appeared. A capsule endoscope, which is swallowed from the mouth of a subject and thereby introduced to the inside of the body, has a function of moving inside body cavities, for example, organs such as the stomach and the small intestine according to peristaltic motion to sequentially pick up images until the capsule endoscope is naturally egested.

During the movement inside the body cavities, data of images picked up by the capsule endoscope inside the body is transmitted to the outside via wireless communication and accumulated in a memory provided inside an external receiver. After a patient swallows a capsule endoscope, the patient is free to do what he/she wants until the capsule endoscope is egested, carrying a receiver having the wireless communication function and the memory function with him/her.

A capsule endoscope obtains drive power from, e.g., a battery incorporated in its casing; however, it is impossible that a user performs an operation to turn on/off driving via, e.g., a switch disposed on an outer face of the casing because of its structure in which, e.g., an internal circuit is also sealed inside the casing. Therefore, capsule endoscopes including a switch inside their casings, the switch being turned on/off according to an external signal, have been proposed.

An in vivo observation system 101 disclosed in Japanese Patent Application Laid-Open Publication No. 2009-89907, which is illustrated in FIG. 1, includes a capsule endoscope 110, a transmission apparatus 102 that transmits an alternating magnetic field signal from the outside of the capsule endoscope 110, and a reception apparatus 103 that receives an image signal from the capsule endoscope 110.

The transmission apparatus 102 includes a power source 102A, a drive section 102B, and a transmission section 102C, which is a magnetic field generating section. The reception apparatus 103 includes an antenna unit 103C, an image receiving section 103B, and an external memory 103A that stores an image.

The capsule endoscope 110 includes a signal receiving section (hereinafter also referred to as "reception section") 111, a control section 121, a battery 119, a switch 125, which is a P-channel FET, and an information acquiring section 126. The information acquiring section 126 includes an illumination unit 128 that emits illuminating light for illuminating an object inside a body, an image pickup unit 127 that picks up an image of the object illuminated by the illumination unit 128 and outputs the image as an image signal, and an RF unit 129 that wirelessly conveys the image signal outputted from the image pickup unit 127 to the outside of the body.

The reception section 111 includes a reception sensor 112 and a reception circuit 113. The reception sensor 112 includes a magnetic field detection coil 112A that outputs an alternating current signal having a magnitude according to a strength of an alternating magnetic field and a resonance capacitor 112B. The reception circuit 113 includes a diode 113A and a capacitor 113B that rectify the alternating current signal outputted from the reception sensor 112 and a resistance 113C.

An output signal S2 from a frequency dividing circuit 122 in the control section 121 is inverted via an output signal S1 from the reception section 111. The switch 125 includes a source connected to the battery 119, a gate connected to an output end of the frequency dividing circuit 122, and a drain connected to the information acquiring section 126.

In the capsule endoscope 110 having the above-described configuration, an alternating magnetic field signal from the signal transmission apparatus 102 is received by the magnetic field detection coil 112A, and based on an internal signal S2 resulting from the received signal being rectified and subjected to frequency division by two in the frequency dividing circuit 122, toggle between supply and stop of power to the information acquiring section 126 is controlled.

SUMMARY OF THE INVENTION

An in vivo information acquiring apparatus according to an embodiment of the present invention includes, inside a capsule casing, an information acquiring section that acquires information on an inside (of a body) of a subject, a power source that supplies power, a detection section that, upon detection of introduction into the inside of the body of the subject, outputs a detection signal, a signal receiving section that receives a control signal from an outside and outputs an internal signal, and a control section that controls power supply from the power source to the information acquiring section according to the internal signal and the detection signal.

DETAILED DESCRIPTION OF THE PREFERRED EMBODIMENT

First Embodiment

A capsule endoscope (hereinafter also referred to as "capsule") 10, which is an in vivo information acquiring apparatus according to a first embodiment of the present invention, will be described below with reference to the drawings.

Figure 1:
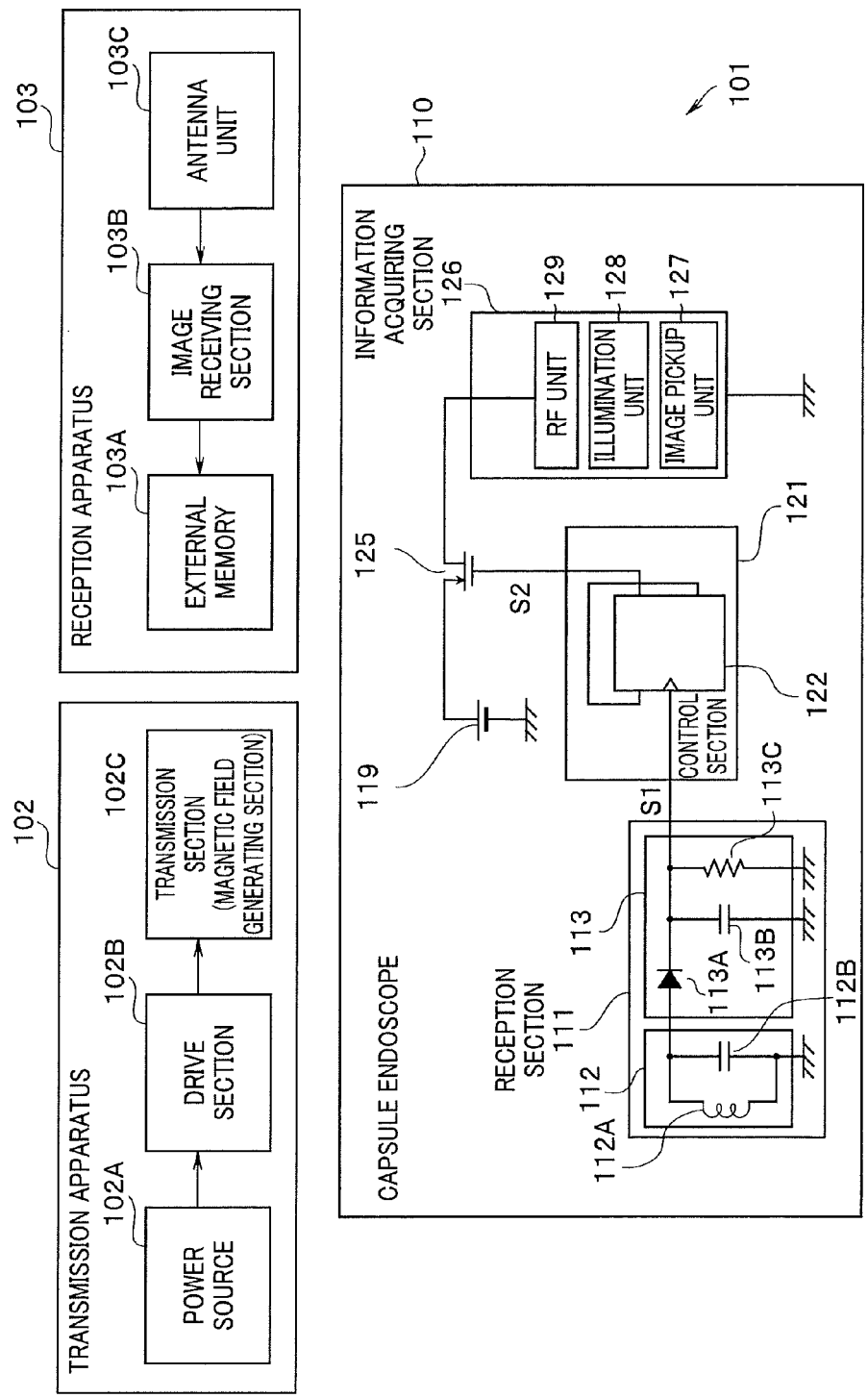
FIG. 1 is a configuration diagram for describing a configuration of a known capsule endoscope.
Figure 2:
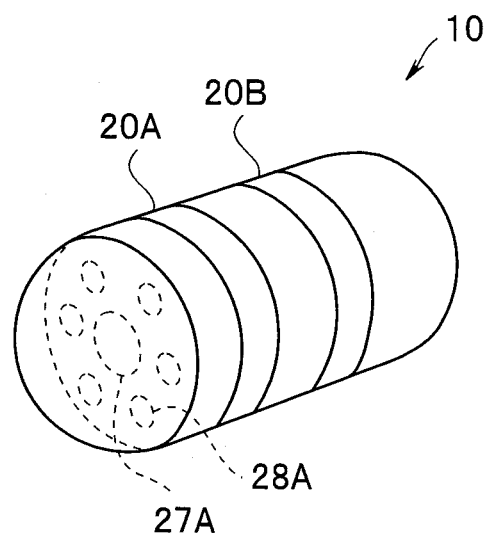
FIG. 2 is a diagram of an outer appearance of a capsule endoscope according to a first embodiment.

As illustrated in FIG. 2, the capsule 10 has a casing having an elongated capsule shape, and an end portion at which an image pickup unit 27A and an illumination unit 28A are disposed has a dome shape formed by a transparent material, and a central cylindrical portion and an opposed dome-shaped end portion are each formed by a light-blocking material. At the central cylindrical portion, an electrode 20A and an electrode 20B are disposed.

When the capsule 10 is outside a body, the electrode 20A and the electrode 20B are isolated from each other, and when the capsule 10 is inside a body, the electrode 20A and the electrode 20B are electrically connected by a body fluid, for example, a gastric fluid. In other words, the capsule 10 includes a detection section 20 (see FIG. 3) that detects an impedance (resistance) between the electrode 20A and the electrode 20B to detect whether or not the capsule 10 is inside a subject (inside a body).

Figure 3:
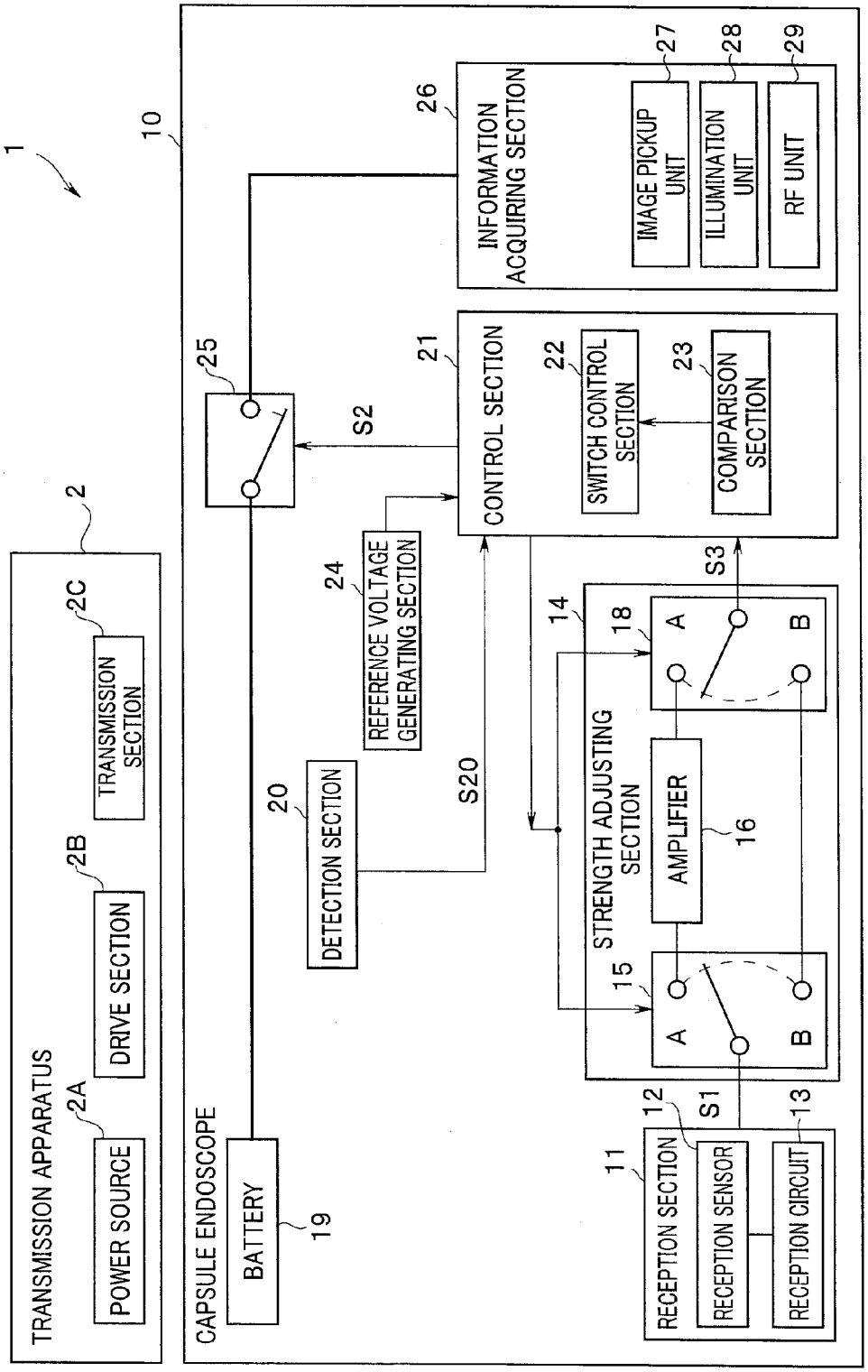
FIG. 3 is a configuration diagram for describing a configuration of the capsule endoscope according to the first embodiment.

Note that, as illustrated in FIG. 3, an in vivo observation system 1 including the capsule 10 and a transmission apparatus 2 has a configuration similar to that of the in vivo observation system 101 that has already been described, and thus, a description of elements having functions similar to those of the in vivo observation system 101 will be omitted. Also, in some of the Figures referred to below, e.g., a reception apparatus is not illustrated. Also, an element described as an independent component may be a part of another component, and a component described as a part of another component may be an independent component.

The capsule 10 includes, inside the capsule casing, the detection section 20, an information acquiring section 26, a reception section 11, which is a signal receiving section, a battery 19, which is a power source, a control section 21, a strength adjusting section 14, a reference voltage generating section 24 and a power source switch 25.

As already described, the detection section 20 includes the electrode 20A and the electrode 20B, and upon detection of introduction of the capsule 10 to the inside of the body of a subject, outputs a detection signal S20. Note that although the electrode 20A and the electrode 20B illustrated in FIG. 2 each have a shape surrounding the cylindrical portion, the electrode 20A and the electrode 20B may each have any shape as long as the shape is a shape that can detect a change in impedance due to introduction to the inside of a body. It is also possible that the detection section 20 includes three or more electrodes and detects electrical connection between any two of the electrodes.

A detection method in the detection section 20 may be one based on, e.g., a temperature sensor, a light sensor, a sound sensor, a pH sensor or an intra-body propagation signal sensor. For example, the sound sensor detects heart sounds peculiar to the inside of a body. Also, the intra-body propagation signal sensor detects a signal generated by a high-frequency signal generating apparatus outside a body and conveyed to the inside of the body via an external electrode disposed on a surface of the body of a subject.

The information acquiring section 26, which acquires information on the inside of the body of a subject, includes the illumination unit 28, the image pickup unit 27 and an RF unit 29. The illumination unit 28 includes, for example, an LED that illuminates a wall surface of an organ inside a body. The image pickup unit 27 includes a solid-state image pickup device such as a CCD or CMOS image sensor that picks up an image of the wall surface of the organ inside the body. The RF unit 29 includes a transmission circuit and a transmission antenna that wirelessly transmit video information obtained by the image pickup unit 27 to the outside of the body. The video information transmitted by the RF unit 29 is accumulated in an external memory in an external reception apparatus (not illustrated).

The signal receiving section 11, which is not illustrated in detail, includes a reception sensor 12 and a reception circuit 13, and receives an alternating magnetic field signal, which is a control signal from the transmission apparatus 2, and outputs a direct current internal signal S1.

The battery 19 is a power source that supplies power used for driving, e.g., the information acquiring section 26. Note that although in the below Figures, only a line of power supply to the information acquiring section 26 is illustrated, the battery 19 supplies power also to the other components.

The power source switch 25 is a power switch including, for example, a P-channel FET, the power switch performing on/off control of the power supply from the battery 19 to the information acquiring section 26. In other words, the power source switch 25 includes a drain connected to the battery 19, a gate connected to an output of the control section 21, and a source connected to the information acquiring section 26. The power source switch 25 performs a toggling operation according to an input of an internal signal S1

The strength adjusting section 14, which includes change-over switches 15 and 18 and an amplifier 16, adjusts a strength of an internal signal S1 outputted by the reception section 11. In other words, the amplifier 16 amplifies the internal signal S1. Note that the change-over switches 15 and 18 are on the B-B side in an initial state.

The control section 21 includes a comparison section 23 and a switch control section 22. The comparison section 23 determines whether or not a strength (voltage) of an internal signal S3 outputted by the reception section 11 and adjusted by the strength adjusting section 14 is higher than a voltage VT of a predetermined voltage signal generated by the reference voltage generating section 24. Then, based on a result of the determination, the comparison section 23 outputs a switch control signal S2 for giving an instruction to maintain or invert the state by toggling control, to the switch control section 22.

Then, the control section 21, upon input of a detection signal S20 from the detection section 20, switches the change-over switches 15 and 18 in the strength adjusting section 14 to the A-A side.

In other words, the control section 21 is a power supply control section that performs control to toggle the power from the battery 19 to the information acquiring section 26 according to the internal signal S3 and the detection signal S20, and also performs overall control of the capsule 10.

The control section 21, upon input of a detection signal S20, performs control so that the strength adjusting section 14 raises the strength of the internal signal S1. In other words, upon detection of introduction to the inside of a body by the detection section 20, the capsule 10 outputs a switch control signal S2 based on an internal signal S3 resulting from amplification by the amplifier 16 that amplifies the strength of the internal signal S1. Thus, the capsule 10 is activated by a weaker control signal when the capsule 10 is inside a body, compared to when the capsule 10 is outside a body.

In other words, when the capsule 10 is outside a body, the capsule 10 is not activated unless the capsule 10 receives a stronger control signal. Accordingly, when the capsule 10 is outside a body, even if a noise signal is applied thereto, the capsule 10 is hard to activate. In other words, the capsule 10 prevents erroneous activation before beginning of use, enabling prevention of battery drain.

Figure 4:
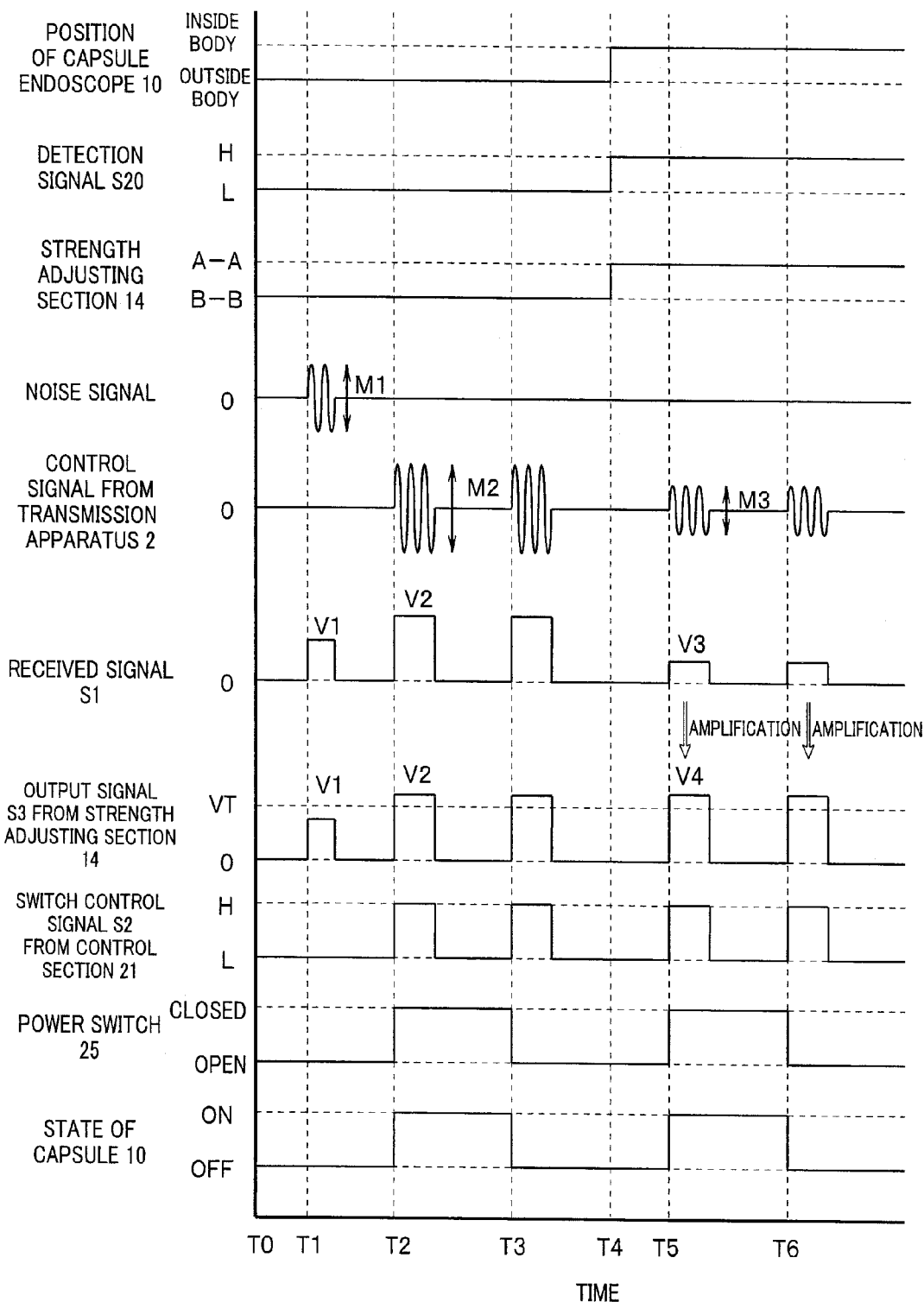
FIG. 4 is a time chart for describing an operation of the capsule endoscope according to the first embodiment.

Next, an operation of the capsule 10 will be described with reference to FIG. 4.

<T0> Initial State

In an initial state, the capsule 10 is arranged outside a body and in a quiescent state (off state) in which the power source switch 25 is in an open state.

In other words, since the capsule 10 is not arranged inside a body, no detection signal S20 from the detection section 20 is outputted. In other words, a detection signal S20 is at an L level.

Accordingly, because the change-over switches 15 and 18 are connected to the B-B side, an internal signal S1 outputted by the reception section 11 is outputted from the strength adjusting section 14 with a strength thereof unchanged and without amplification.

In the comparison section 23, a voltage of an internal signal S3 and the voltage VT of the reference voltage signal are compared. Since no magnetic field signal is transmitted, the internal signal S3 is substantially 0 V and is smaller than the reference voltage signal VT.

Since a switch control signal S2 outputted by the switch control section 22 based on a result of the comparison by the comparison section 23 is at an L level, the power source switch 25 is maintained in an open state. In other words, the capsule 10 is maintained in a quiescent state (off state).

<T1> Noise Signal Input

A case where the reception section 11 in the capsule 10 receives a noise signal with a strength M1 is assumed. The reception section 11, upon receipt of a noise signal with a strength M1, outputs an internal signal S1 with a voltage V1. Here, the change-over switches 15 and 18 are connected to the B-B side, and thus, the internal signal S1 outputted by the reception section 11 is outputted from the strength adjusting section 14 as an output signal S3 with the voltage V1 unchanged and without amplification.

In the comparison section 23, the voltage V1 of the internal signal S3 and the voltage VT of the reference voltage signal are compared. Here, V1<VT. Thus, since the switch control signal S2 outputted by the switch control section 22 is at an L level, the power source switch 25 is maintained in an open state. In other words, the capsule 10 is maintained in a quiescent state (off state).

In other words, when the capsule 10 is outside a body, the capsule 10 does not erroneously operate due to a noise signal generating an internal signal S1 that is smaller than the voltage VT of the reference voltage signal to enter an activated state (on state).

<T2> Control Signal Input

Upon receipt of a control signal with a strength M2 from the transmission apparatus 2, the reception section 11 outputs an internal signal S1 with a voltage V2. Then, in the comparison section 23, the voltage V2 of the internal signal S3 and the voltage VT of the reference voltage signal are compared. Here, V2>VT. Accordingly, the switch control section 22 in the control section 21 outputs an H-level switch control signal S2. Accordingly, the power source switch 25 enters a closed state, and thus, power from the battery 19 is supplied to the information acquiring section 26, and the capsule 10 enters an activated state (on state).

The information acquiring section 26 in an activated state picks up an image at predetermined time intervals, and wirelessly transmits the picked-up image. The image signal transmitted by the RF unit 29 is checked via a reception apparatus (not illustrated), whereby normal operation of the capsule 10 is confirmed.

<T3> Control Signal Input

Upon receipt of a control signal with a strength M2 from the transmission apparatus 2 again, the switch control section 22 in the control section 21 outputs an H-level switch control signal S2. Then, the power source switch 25 enters an open state, and thus, the capsule 10 enters a quiescent state (off state) again. In other words, each time an internal signal S3 is inputted to the control section 21, the control section 21 performs a toggling operation.

<T4> Introduction to Inside of Body

The capsule 10 is swallowed and introduced to the inside of a body of a subject. Then, the electrode 20A and the electrode 20B are connected via, e.g., a gastric fluid, whereby the detection section 20 detects the introduction to the inside of the body of the subject, and outputs a detection signal S20. In other words, the detection signal S20 turns from an L level to an H level. The control section 21 performs control based on the detection signal S20 so as to switch the change-over switches 15 and 18 in the strength adjusting section 14 to the A-A side.

Then, an internal signal S3 resulting from an internal signal S1 outputted by the reception section 11 being amplified by the amplifier 16 is inputted to the control section 21. Note that an amplification factor of the amplifier 16 is set according to the condition before use (swallow) and the use conditions. As described later, when the capsule 10 is introduced to the inside of the body, a distance between the capsule 10 and the transmission apparatus 2 becomes long, and the control signal is attenuated by body tissues existing in the transmission path. Thus, at least amplification processing for amplifying a received signal S1 to a strength enabling the capsule 10 inside the body to be controlled via a control signal generated by the transmission apparatus 2 is necessary.

<T5> Control Signal Input

Upon receipt of a control signal with a strength M3 from the transmission apparatus 2, the reception section 11 outputs an internal signal S1 with a voltage V3. In other words, the strength M3 of the control signal received by the capsule 10 inside the body is smaller than the strength M2 of the control signal received outside the body. Furthermore, here, a case where the strength M3 is smaller than the strength M1 of the noise signal is assumed. In other words, a relationship among the voltages of the internal signal S1 outputted by the reception section 11 is V2>V1>V3.

However, since the change-over switches 15 and 18 in the strength adjusting section 14 is switched to the A-A side, the internal signal S1 with the voltage V3 is amplified by the amplifier 16 and the voltage becomes V4. In other words, an amplification factor of the amplifier 16 is V4/V3.

Then, in the comparison section 23, the voltage V4 of the internal signal S3 and the voltage VT of the reference voltage signal are compared. Here, V4>VT. Accordingly, the switch control section 22 in the control section 21 outputs an H-level switch control signal S2. Accordingly, the power source switch 25 enters a closed state, and thus, power from the battery 19 is supplied to the information acquiring section 26, whereby the capsule 10 is activated.

In other words, in the capsule 10, even a control signal with the strength M3, which is smaller than a noise signal with the strength M1 that does not function as an activation signal outside the body, functions as a control signal inside the body. Accordingly, it is not necessary to increase a strength of a magnetic field signal to be transmitted, in order to control the capsule 10 inside the body via the transmission apparatus 2.

The information acquiring section 26 in an activated state picks up an image at predetermined time intervals, and wirelessly transmits an image signal. The image signal transmitted by the RF unit 29 is received by a reception apparatus and stored in the external memory.

<T6> Control Signal Input

Upon receipt of a control signal with the strength M3 from the transmission apparatus 2 again, the switch control section 22 in the control section 21 outputs an H-level switch control signal S2. Then, the power source switch 25 enters an open state, and the capsule 10 enters a quiescent state again.

In other words, control to turn on/off the capsule 10 that is inside the body can also be performed via a control signal.

As described above, during a period (T0 to T4) in which the capsule 10 is arranged outside the body, the strength adjusting section 14 selects a path (B-B) in which the internal signal S1 is not amplified, and thus, the state of the power source switch 25 is insusceptible to a noise signal. On the other hand, after the capsule 10 is arranged inside the body (T4 onwards), the strength adjusting section 14 selects a path (A-A) in which the internal signal S1 is amplified, and thus, even with a weak control signal, the power source switch 25 can be controlled. In other words, the capsule 10 has no possibility of erroneous activation/erroneous stoppage, enabling prevention of battery drain.

Modifications 1 to 4 of First Embodiment

Next, capsule endoscopes 10A to 10D according to modifications 1 to 4 of the first embodiment of the present invention will be described. The capsule endoscopes 10A to 10D are similar to the capsule endoscope 10 and thus only differences between each of the capsule endoscopes 10A to 10D and the capsule endoscope 10 will be described.

Figure 5A:
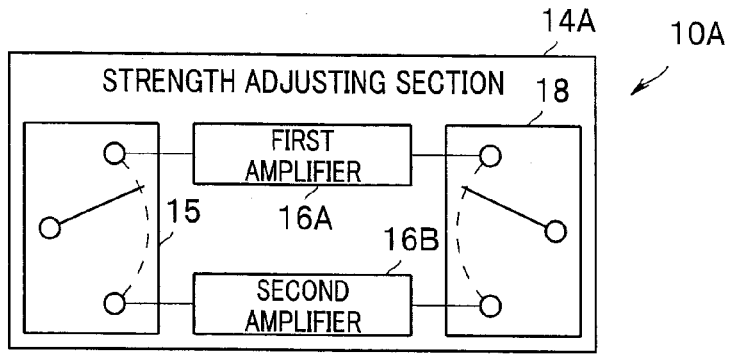
FIG. 5A is a configuration diagram for describing a configuration of a strength amplifying section in a capsule endoscope according to modification 1 of the first embodiment.

As illustrated in FIG. 5A, a strength adjusting section 14A in the capsule endoscope 10A according to modification 1 includes a first amplifier 16A and a second amplifier 16B with an amplification factor that is larger than that of the first amplifier 16A, and a gain of an internal signal S1, that is, a strength of an internal signal S3 to be outputted can be adjusted via change-over switches 15 and 18.

A control section 21 performs control so that the internal signal S1 is amplified by the first amplifier 16A when the capsule 10A is outside a body, and the internal signal S1 is amplified by the second amplifier 16B when the capsule 10A is inside a body.

For example, even when the capsule 10A is outside a body, even if a magnitude of an internal signal S1 outputted by the reception section 11 is small and an internal signal strength V2 is smaller than a voltage VT of a reference voltage signal, the internal signal S1 can be amplified to be equal to or larger than the voltage VT of the reference voltage signal.

Note that the amplification factor of the amplifier 16A, a bare minimum value necessary for preventing activation by a noise signal is arbitrarily set.

The capsule 10A according to the present modification provides the effects provided by the capsule 10, and also enables reliable on/off control even if the strength of the internal signal S1 outputted by the reception section 11 outside a body is small.

Figure 5B:
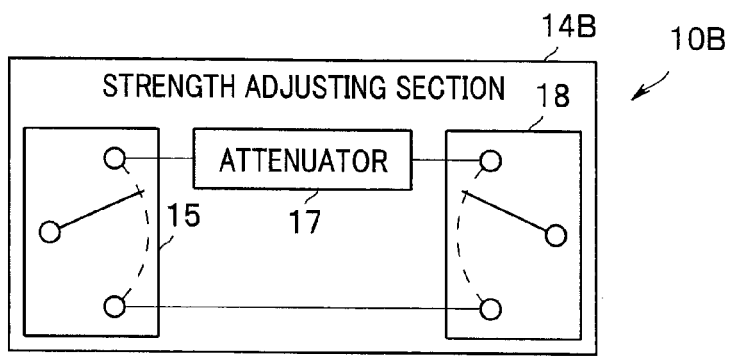
FIG. 5B is a configuration diagram for describing a configuration of a strength amplifying section in a capsule endoscope according to modification 2 of the first embodiment.

Next, as illustrated in FIG. 5B, a strength adjusting section 14B in the capsule endoscope 10B according to modification 2 includes an attenuator 17, and can adjust a strength of an internal signal S1 via change-over switches 15 and 18.

An attenuation factor of the attenuator 17 is set according to the use conditions as with, e.g., the amplification factor of the amplifier 16 in the first embodiment, which has already been described.

A control section 21 performs control so that the internal signal S1 is attenuated by the attenuator 17 when the capsule 10B is outside a body and the internal signal S1 is outputted as it is when the capsule 10B is inside a body. Accordingly, the capsule 10B is hard to activate by a noise signal.

The capsule 10B according to the present modification provides the effects provided by the capsule 10, and furthermore, is hard to erroneously activate even when the strength of the internal signal S1 outputted by the reception section 11 outside a body is large.

Figure 5C:
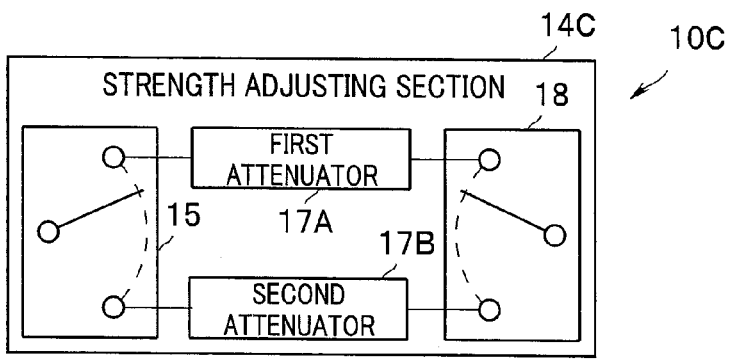
FIG. 5C is a configuration diagram for describing a configuration of a strength amplifying section in a capsule endoscope according to modification 3 of the first embodiment.

Next, as illustrated in FIG. 5C, a strength adjusting section 14C in the capsule endoscope 10C according to modification 3 includes a first attenuator 17A, and a second attenuator 17B with an attenuation factor that is smaller than that of the first attenuator 17A, and can adjust a strength of an internal signal S1 via change-over switches 15 and 18.

The control section 21 performs control so that the internal signal S1 is attenuated by the first attenuator 17A when the capsule 10C is outside a body and the internal signal S1 is attenuated by the second attenuator 17B when the capsule 10C is inside a body.

The capsule 10C according to the present modification provides the effects provided by the capsule 10, and furthermore, is hard to erroneously activate even if the strength of the internal signal S1 outputted by a reception section 11 is large.

Figure 5D:
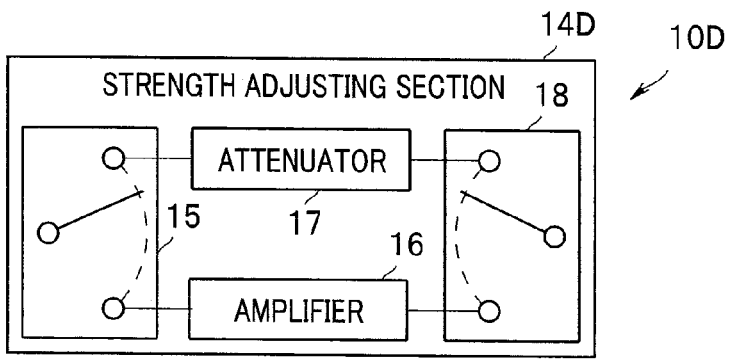
FIG. 5D is a configuration diagram for describing a configuration of a strength amplifying section in a capsule endoscope according to modification 4 of the first embodiment.

Next, as illustrated in FIG. 5D, a strength adjusting section 14D in the capsule endoscope 10D according to modification 4 includes an attenuator 17 and an amplifier 16, and can adjust a strength of an internal signal S1 via change-over switches 15 and 18.

A control section 21 performs control so that the internal signal S1 is attenuated by the attenuator 17 when the capsule 10D is outside a body and the internal signal S1 is amplified by the amplifier 16 when the capsule 10D is inside a body.

The capsule 10D according to the present modification provides the effects provided by the capsule 10, and furthermore, can reliably perform on/off control without erroneous operation even if a strength of an internal signal outputted by a reception section 11 when the capsule 10D is outside a body is large and a strength of an internal signal outputted by the reception section 11 when the capsule 10D is inside a body is small.

Second Embodiment

Next, a capsule endoscope 10E according to a second embodiment of the present invention will be described. Since the capsule endoscope 10E is similar to the capsule endoscope 10, only differences therebetween will be described.

Figure 6:
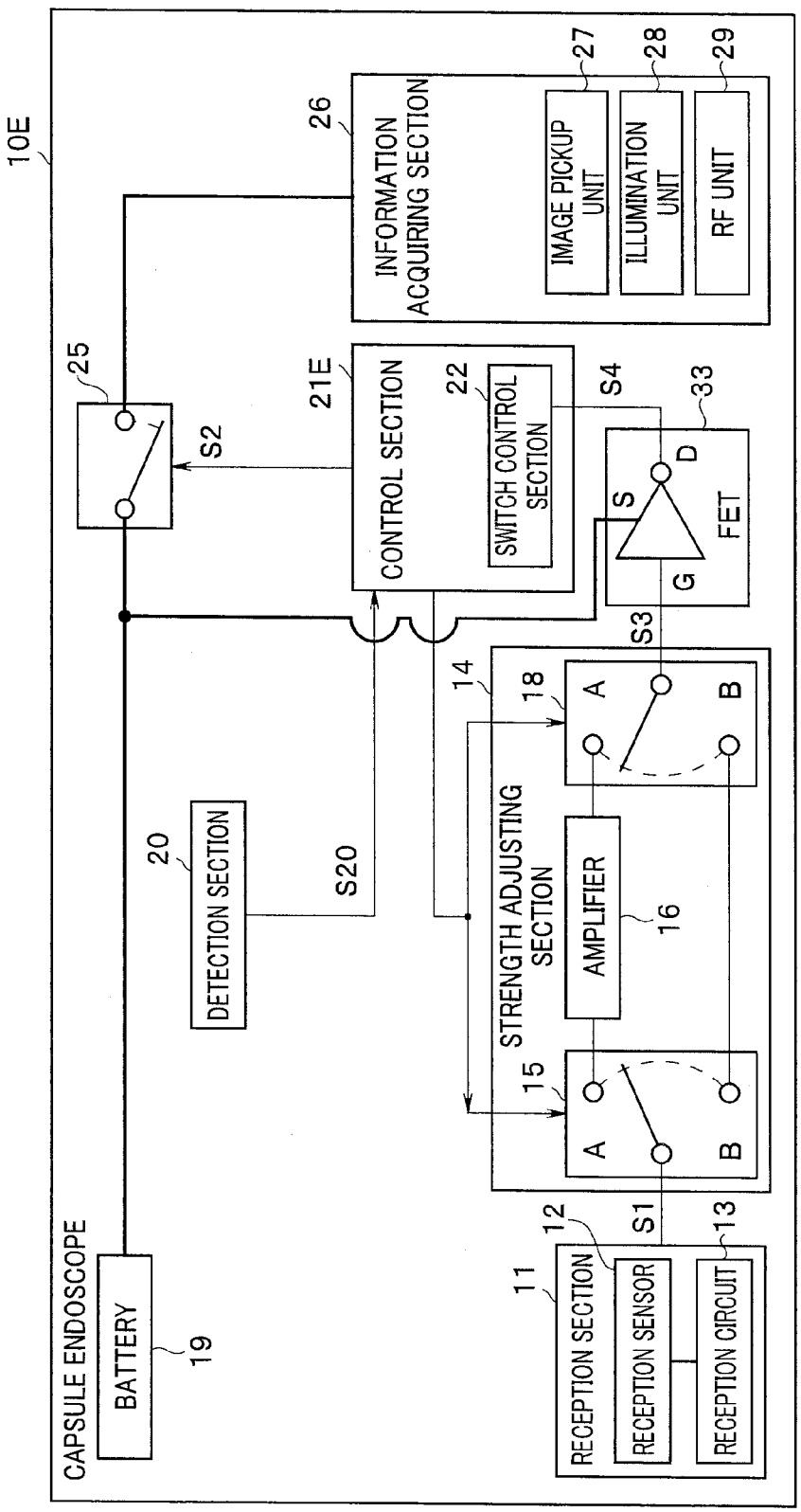
FIG. 6 is a configuration diagram for describing a configuration of a capsule endoscope according to a second embodiment.

As illustrated in FIG. 6, the capsule endoscope 10E includes a field-effect transistor (FET) 33 instead of the reference voltage generating section and the comparison section. The FET 33, which is an inverter circuit, outputs a voltage inputted to an S terminal to a D terminal where a voltage of an internal signal S3 inputted to a G terminal is larger than a predetermined threshold value. In other words, a voltage of a signal S4 outputted to a control section 21E varies according to the internal signal S3.

The capsule endoscope 10E according to the present embodiment provides the effects provided by the capsule endoscope 10 and furthermore, has a simple configuration. Note that the configuration of the capsule endoscope 10E can also be used for the capsules 10A to 10D, which have been already described.

Third Embodiment

Next, a capsule endoscope 10F according to a third embodiment of the present invention will be described. Since the capsule endoscope 10F is similar to the capsule endoscope 10, only differences therebetween will be described.

Figure 7:
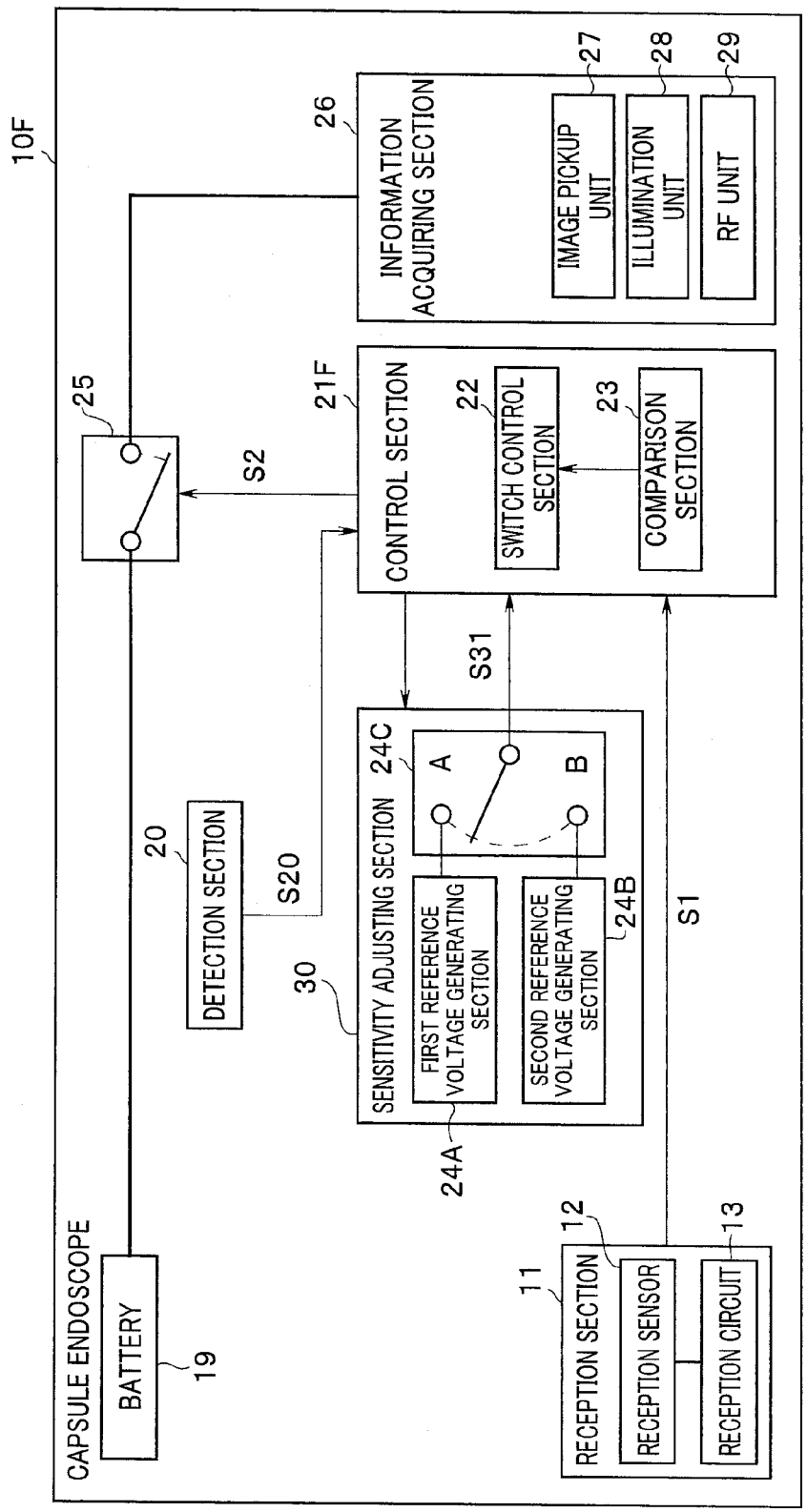
FIG. 7 is a configuration diagram for describing a configuration of a capsule endoscope according to a third embodiment.

As illustrated in FIG. 7, the capsule endoscope 10F includes a sensitivity adjusting section 30 that includes a first reference voltage generating section 24A, a second reference voltage generating section 24B, and a switch 24C that switches between reference voltages to be outputted.

As already described, a control section performs control according to an internal signal with a strength exceeding a predetermined threshold value. In other words, the comparison section 23 compares a comparison voltage, which is a predetermined threshold value, and an internal signal, and based on a result of the comparison, the control section performs control.

In the capsule endoscope 10 according to the first embodiment, the strength adjusting section 14 adjusts (increases/decreases) the strength of the internal signal S1. On the other hand, in the capsule endoscope 10F according to the present embodiment, the sensitivity adjusting section 30 adjusts (increases/decreases) a reference voltage.

In other words, a first reference voltage VTA generated by the first reference voltage generating section 24A is higher than a second reference voltage VTB generated by the second reference voltage generating section 24B. Then, a control section 21F controls the switch 24C in the sensitivity adjusting section 30 so that the first reference voltage VTA is outputted from the sensitivity adjusting section 30 when the capsule 10F is outside a body (detection signal S20: L level) and the second reference voltage VTB that is lower than the first reference voltage VTA is outputted when the capsule 10F is inside a body (detection signal S20: H level).

As with, e.g., the amplification factor of the amplifier 16, which has already been described in the first embodiment, the first reference voltage VTA and the second reference voltage VTB are set according to the conditions before use (swallow) and the use conditions.

The capsule 10F according to the present embodiment provides effects that are the same as those of the capsule 10.

Fourth Embodiment

Next, a capsule endoscope 10G according to a fourth embodiment of the present invention will be described. Since the capsule endoscope 10G is similar to the capsule endoscope 10, only differences therebetween will be described.

Figure 8:
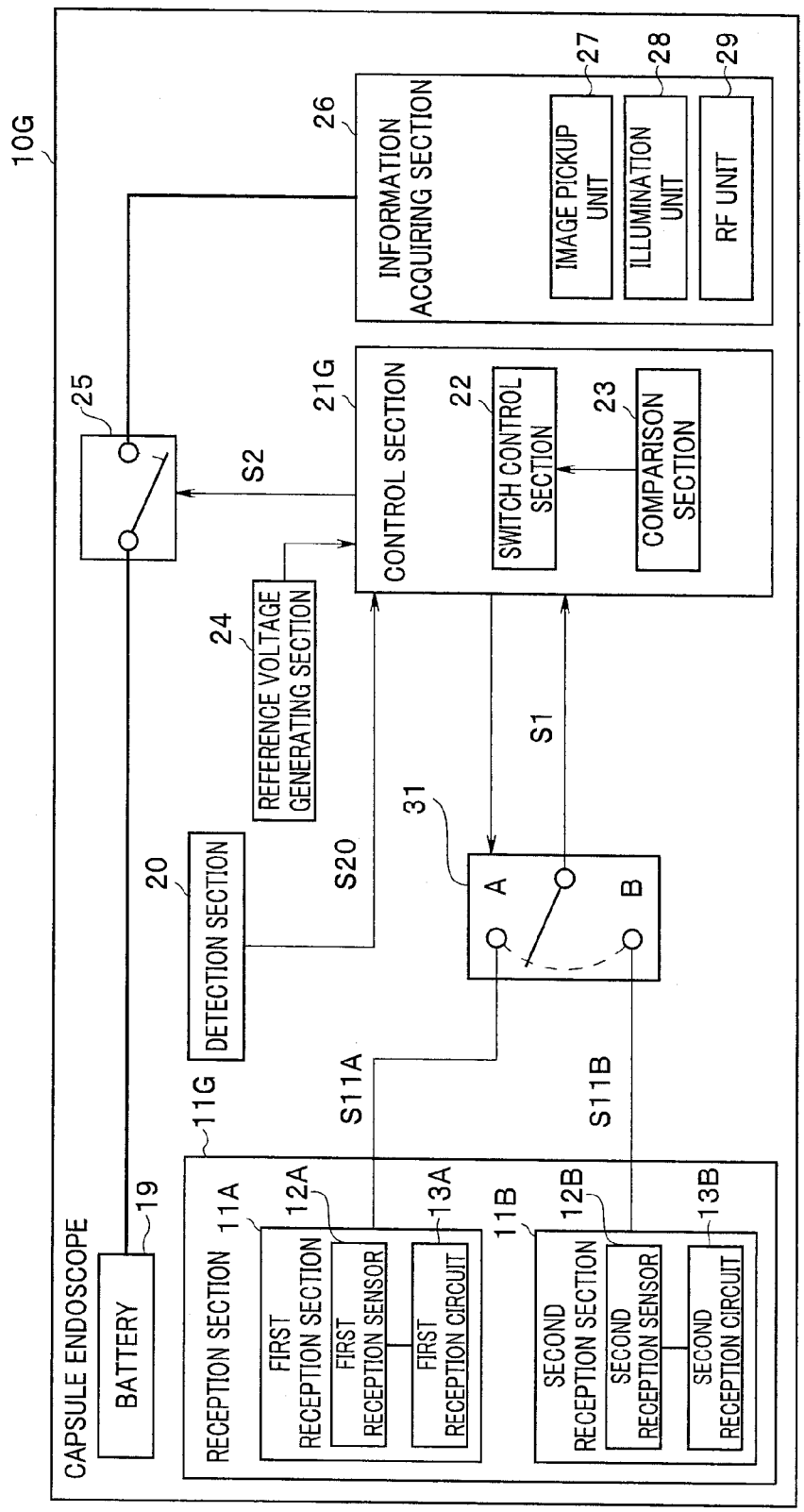
FIG. 8 is a configuration diagram for describing a configuration of a capsule endoscope according to a fourth embodiment.

As illustrated in FIG. 8, in the capsule endoscope 10G, a signal receiving section 11G includes a first signal receiving section 11A that receives a first control signal from the outside and outputs a first internal signal S11A, a second signal receiving section 11B that receives a second control signal from the outside and outputs a second internal signal S11B, and a switch 31 via which the first internal signal S11A or the second internal signal S11B is selected as an internal signal S1. Note that the first signal receiving section 11A includes a first reception sensor 12A and a first reception circuit 13A, and the second signal receiving section 11B includes a second reception sensor 12B and a second reception circuit 13B.

For example, the number of turns of a magnetic field detection coil in the second reception sensor 12B is larger than that of the first reception sensor 12A. Accordingly, even if the second signal receiving section 11B receives a signal with a strength that is the same as that of a signal received by the first signal receiving section 11A, the second signal receiving section 11B outputs an internal signal that is stronger than that of the first signal receiving section 11A.

Then, a control section 21G controls the switch 31 according to a detection signal S20 from the detection section 20. In other words, when the capsule endoscope 10G is outside a body, the first internal signal S11A is inputted to a comparison section 23 as an internal signal S1, and when the capsule endoscope 10G is inside a body, the second internal signal S11B is inputted to the comparison section 23 as the internal signal S1.

The comparison section 23 compares the internal signal S1 selected via the switch 31 (the first internal signal S11A or the second internal signal S11B), and a reference voltage VT.

In other words, when the capsule endoscope 10G is outside a body (detection signal S20: L level), the first signal receiving section 11A, which outputs a small internal signal S11A, is used, and when the capsule endoscope 10G is introduced to the inside of a body (detection signal S20: H level), the second signal receiving section 11B, which outputs a strong internal signal S11B, is used.

Accordingly, the capsule 10G according to the present embodiment, which includes a plurality of signal receiving sections, provides effects that are the same as those of the capsule 10.

Note that in a modification of the capsule 10G, control signals received by the first signal receiving section 11A and the second signal receiving section 11B in the reception section 11G may be different types of physical energies. For example, it is possible that a control signal received by the first signal receiving section 11A when the capsule is outside a body is an optical signal and a control signal received by the second signal receiving section 11B when the capsule is inside a body is a magnetic field signal.

The capsule according to the modification, which includes a plurality of signal receiving sections that respectively receive different types of signals, provides effects that are the same as those of the capsule 10G, and furthermore, is hard to erroneously operate.

Fifth Embodiment

Next, a capsule endoscope 10H according to a fifth embodiment of the present invention will be described. Since the capsule endoscope 10H is similar to the capsule endoscope 10G, only differences therebetween will be described.

Figure 9:
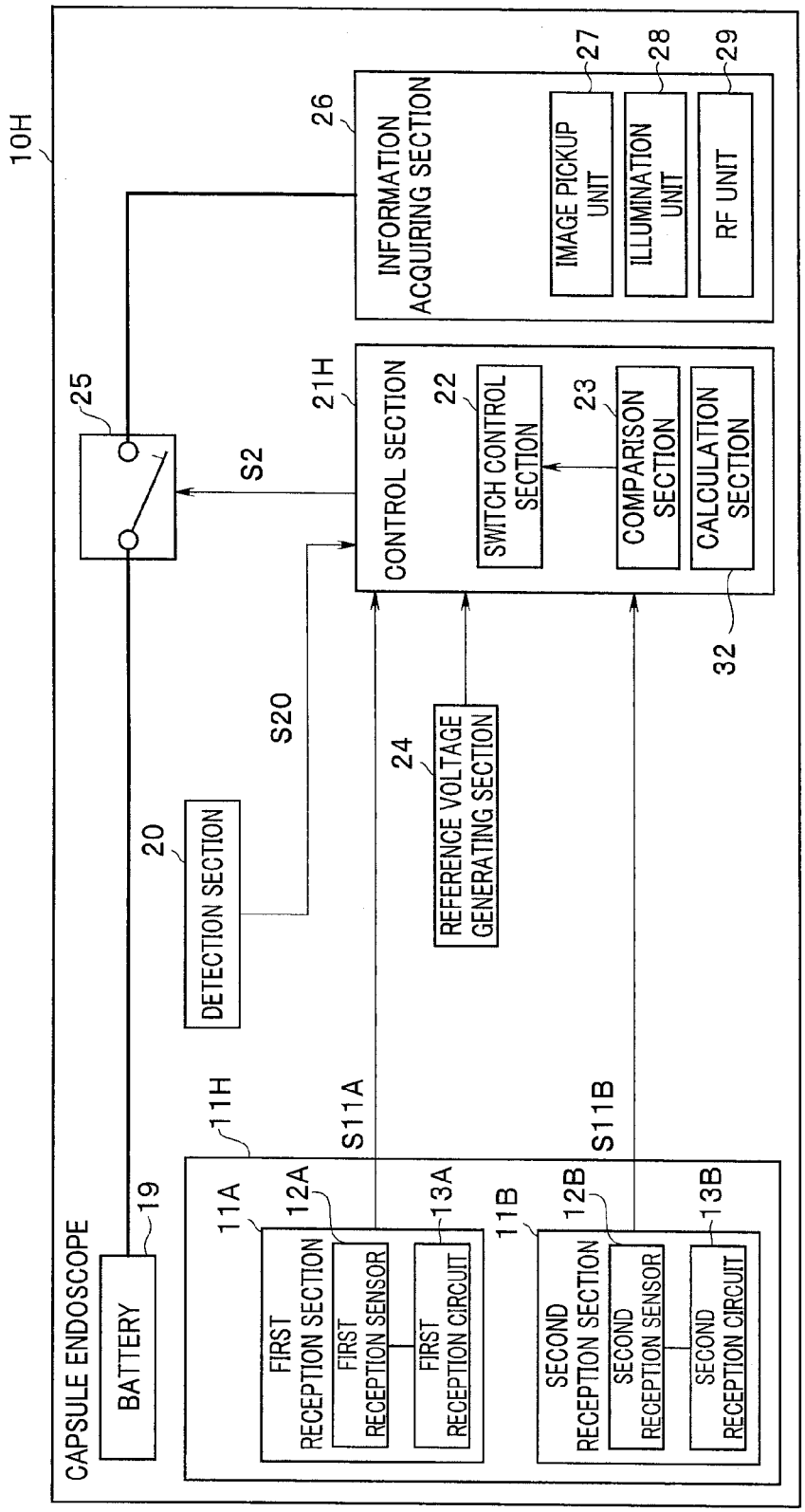
FIG. 9 is a configuration diagram for describing a configuration of a capsule endoscope according to a fifth embodiment.

As illustrated in FIG. 9, in the capsule endoscope 10H, a control section 21H includes a calculation section 32 that generates an internal signal S2 based on a first internal signal S11A and a second internal signal S11B.

When no detection signal S20 is inputted to the calculation section 32, upon a simultaneous input of both signals, i.e., the first internal signal S11A and the second internal signal S11B, the calculation section 32 controls an output of the internal signal S2. On the other hand, when a detection signal S20 is inputted to the calculation section 32, upon input of at least either signal of the first internal signal S11A and the second internal signal S11B, the calculation section 32 controls the output of the internal signal S2.

In other words, the calculation section 32 controls the output of the internal signal S2 according to a logical product of the two internal signals S11A and S11B when the capsule endoscope 10H is outside a body and controls the output of the internal signal S2 according to a logical sum of the two internal signals S11A and S11B when the capsule endoscope 10H is inside a body.

Then, respective directions of control signal detection by the first signal receiving section 11A and the second signal receiving section 11B in the reception section 11H are orthogonal to each other. In other words, directions of magnetic field detection by respective magnetic field detection coils are orthogonal to each other.

For example, when no detection signal S20 is inputted, if strengths of signals received by the first internal signal S11A and the second internal signal S11B both exceed a voltage VT of a reference voltage signal, a switch control signal S2 provides a toggling operation. In other words, unless control signals are applied from two directions, the operating state of a switch 25 does not change.

On the other hand, when a detection signal S20 is inputted, if at least either of the strength of the first internal signal S11A and the strength of the second internal signal S11B exceeds the voltage VT of the reference voltage signal, the switch control signal S2 provides a toggling operation.

A position of the capsule 10H inside a body cannot be figured out. However, since control signals from two directions can efficiently be received, the capsule 10H can easily be controlled even when the capsule 10H is inside a body. Furthermore, a larger one of the first internal signal S11A and the second internal signal S11B may be used for the control or a synthesized signal obtained by addition of the first internal signal S11A and the second internal signal S11B may be used for the control.

The capsule 10H according to the present embodiment provides effects that are the same as those of the capsule 10G and furthermore more reliably prevents erroneous activation, enabling prevention of battery drain.

Furthermore, in modification 1 of the capsule 10H, it is possible that the control section 21H in the capsule endoscope 10H controls an output of an internal signal S2 only according to a first internal signal S11A when no detection signal S20 is inputted and according to at least either of the first internal signal S11A and the second internal signal S11B when a detection signal is inputted.

Note that in modification 2 of the capsule 10H, it is possible that the capsule further includes a third signal receiving section that efficiently receives a magnetic field in a direction orthogonal to the directions of magnetic field detections by the first signal receiving section 11A and the second signal receiving section 11B, and a control section performs control only according to a first internal signal when the capsule is outside a body and according to any one of internal signals or a synthesized signal of three internal signals.

Furthermore, in modification 3 of the capsule 10H, control signals received by the first signal receiving section 11A and the second signal receiving section 11B may be different types of physical energies.

Note that in a modification of the capsule 10G, it is possible that the capsule further includes a third signal receiving section that efficiently receives a magnetic field in a direction orthogonal to those of the first signal receiving section 11A and the second signal receiving section 11B, and a control section performs control only according to a first internal signal when the capsule is outside a body and according to any one of internal signals or a synthesized signal of three internal signals.

Furthermore, in a modification of the capsule 10G, control signals received by the first signal receiving section 11A and the second signal receiving section 11B may be different types of physical energies.

Although the above description has been provided taking a capsule endoscope as an example of an in vivo information acquiring system, an in vivo information acquiring system according to the present invention can be applied to various types of capsule in vivo information acquiring apparatuses such as capsule medical apparatuses for digestive organ fluid collection, capsule pH sensors and capsule temperature sensors.

The present invention is not limited to the above-described embodiments and modifications, and combinations of the embodiments and modifications, various variations, alterations and the like are possible without departing from the spirit of the present invention.

What is claimed is:
1. An in vivo information acquiring apparatus comprising, inside a capsule casing,
   a first sensor that acquires information on an inside of a body of a subject,
   a power source that supplies power,
   a second sensor that, upon detection of introduction of the capsule casing into the inside of the body of the subject, outputs a detection signal,
   a receiver that receives a control signal from an outside and outputs an internal signal,
   a strength adjusting section that adjusts a strength of the internal signal, and
   a controller comprising hardware to which the detection signal and internal signal are input, the controller controlling power supply from the power source to the first sensor and the strength adjusting section according to the internal signal and the detection signal.
2. The in vivo information acquiring apparatus according to claim 1, wherein upon input of the detection signal, the controller controls the strength adjusting section so as to raise the strength of the internal signal.

3. The in vivo information acquiring apparatus according to claim 2, wherein the strength adjusting section includes an amplification section that raises the strength of the internal signal.

4. The in vivo information acquiring apparatus according to claim 2, wherein the strength adjusting section includes an attenuation section that lowers the strength of the internal signal.

5. The in vivo information acquiring apparatus according to claim 1,
wherein the receiver includes a first signal receiving section that receives a first control signal from the outside and outputs a first internal signal, and a second signal receiving section that receives a second control signal from the outside and outputs a second internal signal; and
wherein the controller performs control according to the detection signal and at least either of the first internal signal and the second internal signal.

6. The in vivo information acquiring apparatus according to claim 5, wherein the controller performs control according to the first internal signal or the second internal signal selected based on the detection signal.

7. The in vivo information acquiring apparatus according to claim 5, wherein
the controller performs control
only according to the first internal signal when the detection signal is not inputted, and
according to the first internal signal or the second internal signal when the detection signal is inputted.

8. The in vivo information acquiring apparatus according to claim 1, wherein the second sensor is two or more electrodes spaced apart on an exterior surface of the capsule casing.

9. The in vivo information acquiring apparatus according to claim 1, wherein the first sensor is at least an image sensor.

10. The in vivo information acquiring apparatus according to claim 1,
wherein the strength adjusting section comprises an amplifier that amplifies the internal signal and a change-over switch that switches connection to the amplifier, and
the controller controls the change-over switch according to the internal signal.

11. An in vivo information acquiring apparatus comprising, inside a capsule casing,
a first sensor that acquires information on an inside of a body of a subject,
a power source that supplies power,
a second sensor that, upon detection of introduction of the capsule casing into the inside of the body of the subject, outputs a detection signal,
a receiver that receives a control signal from an outside and outputs an internal signal,
a controller comprising hardware to which the detection signal and internal signal are input, the controller controlling power supply from the power source to the first sensor according to the internal signal having a strength exceeding a threshold value, and
a sensitivity adjusting section that one of increases or decreases the threshold value according to the detection signal.

12. The in vivo information acquiring apparatus according to claim 11, wherein upon input of the detection signal, the controller performs control so that the sensitivity adjusting section decreases the threshold value.

13. The in vivo information acquiring apparatus according to claim 11,
wherein the sensitivity adjusting section comprises a first reference voltage generating section that outputs a first reference voltage, a second reference voltage generating section that outputs a second reference voltage and a switch that switches connection with the first reference voltage generating section and connection with the second reference voltage generating section, and
the controller switches the switch based on the internal signal.

* * * * *